United States Patent [19]

Ledley et al.

[11] Patent Number: 4,716,225
[45] Date of Patent: Dec. 29, 1987

[54] RADIOOPAQUE SUGAR DERIVATIVES AND A METHOD OF METABOLIC MAPPING USING THE SAME

[75] Inventors: Robert S. Ledley, Silver Spring, Md.; Douglas M. Gersten, Washington, D.C.

[73] Assignee: Georgetown University, Washington, D.C.

[21] Appl. No.: 781,494

[22] Filed: Sep. 30, 1985

Related U.S. Application Data

[63] Continuation-in-part of Ser. No. 685,227, Dec. 27, 1984, which is a continuation of Ser. No. 385,730, Jun. 7, 1982, abandoned.

[51] Int. Cl.[4] .................. A61K 31/70; A61K 49/04
[52] U.S. Cl. .................................... 536/122; 424/5; 514/23
[58] Field of Search ............... 424/5; 536/122; 514/23

[56] References Cited

U.S. PATENT DOCUMENTS 2,365,776  12/1944  Raymond et al. ............... 424/5
2,365,777  12/1944  Raymond et al. ............... 424/5

Primary Examiner—Ronald W. Griffin
Attorney, Agent, or Firm—Oblon, Fisher, Spivak, McClelland & Maier

[57] ABSTRACT

A method of metabolically mapping one or more central nervous system components of a mammalian body by computerized axial tomography scanning which entails injecting an effective amount of a 2-, 5- or 6-iodo-substituted hexose, as a contrast medium, into the mammalian body, and scanning the mammalian body by computerized axial tomography, thereby visualizing the concentration flux of said hexose in the central nervous system component or components.

19 Claims, 12 Drawing Figures

|     |     |     |     |     |     |     |     |
|-----|-----|-----|-----|-----|-----|-----|-----|
| 7   | 6   | 5   | 13  | 21  | 55  | 255 | 255 |
| 11  | 14  | 15  | 21  | 52  | 255 | 255 | 255 |
| 11  | 19  | 25  | 57  | 255 | 255 | 255 | 255 |
| 16  | 25  | 59  | 255 | 255 | 255 | 255 | 255 |
| 23  | 59  | 255 | 255 | 255 | 255 | 255 | 255 |
| 51  | 255 | 255 | 255 | 255 | 255 | 255 | 255 |
| 255 | 255 | 255 | 255 | 255 | 255 | 255 | 255 |
| 255 | 255 | 255 | 255 | 255 | 255 | 255 | 255 |
| 255 | 255 | 255 | 255 | 255 | 255 | 255 | 81  |
| 255 | 255 | 255 | 255 | 255 | 82  | 39  | 18  |
| 255 | 255 | 255 | 105 | 48  | 25  | 16  | 11  |
| 255 | 255 | 85  | 28  | 13  | 11  | 10  | 10  |
| 255 | 79  | 24  | 10  | 5   | 1   | 1   | 5   |
| 107 | 27  | 13  | 8   | 3   | 1   | 3   | 5   |
| 45  | 17  | 10  | 4   | 4   | 6   | 7   | 5   |
| 23  | 14  | 8   | 2   | 3   | 6   | 6   | 3   |
| 17  | 11  | 6   | 3   | 3   | 3   | 2   | 1   |
| 15  | 7   | 3   | 4   | 5   | 4   | 0   | 0   |
| 15  | 6   | 2   | 5   | 8   | 6   | 2   | 1   |
| 11  | 3   | 2   | 7   | 9   | 4   | 0   | 1   |
| 9   | 1   | 0   | 4   | 7   | 4   | 0   | 0   |
|     | 4   | 1   | 2   | 6   | 6   | 3   | 0   |
|     | 3   | 4   | 6   | 6   | 3   | 1   | 0   |
|     | 4   | 3   | 6   | 9   | 4   | 0   | 0   |
| 9   | 2   | 0   | 4   | 10  | 8   | 1   | 0   |

FIG. 7  WATER PHANTOM "B"

FIG. 8

RADIOOPAQUE SUGAR DERIVATIVES AND A METHOD OF METABOLIC MAPPING USING THE SAME

This application is a continuation-in-part of U.S. patent application Ser. No. 685,227, filed on Dec. 27, 1984 which is a file wrapper continuation of U.S. patent application Ser. No. 385,730, filed on June 7, 1982, now abandoned.

BACKGROUND OF THE INVENTION

1. Field of the Invention

The present invention relates to certain radioopaque hexoses visualizable by computerized axial tomography (CAT) scanning and, more particularly, to a method of metabolic mapping using the same.

2. Description of the Background

With an increased understanding of cerebral energetics, it has become clear that cerebral function and energy metabolism are linked. Thus, knowledge of the rate of energy consumption or utilization should provide a significant insight into cerebral function both at the level of the whole brain and of the individual structures therein.

The energy requirements of nervous tissue, in general, are high. In fact, nervous tissue has a rate of oxidative metabolism which is almost as great as tissues which participate in processes requiring inordinate amounts of energy, such as mechanical work, osmotic work or extensive biosynthesis. See *Cerebral Energy Metabolism and Metabolic Encephalopathy*, Edited by D. W. McCandless.

Although glucose is not the only source of cerebral energy, it is the major source. Investigations involving glucose transport across the bloodbrain barrier have suggested that a significant correlation, by region, exists between glucose influx and utilization. See McCandless, id. This seems to suggest that the glucose supply provided to individual cerebral structures is in accordance with their respective metabolic requirements.

A technique allowing the determination of the rate of flux of such nutrients into specific anatomical structures of the brain would be expected to provide a window to a most dynamic process. As applied to a human brain, such a technique would, in essence, provide a potential bridge across the heretofore unbridgeable conceptual gap between the brain as a physical object and mental consciousness. Up until the present, subtle changes in consciousness have been, necesarily, inferred circumstantially from the effects of drugs, for example, believed to act upon the brain. While some efforts have been made to establish correlations between brain function, structure and consciousness, the underlying linking principles remain unknown.

To be sure, some attempts have been made to metabolically map the mammalian central nervous system. However, the principal means utilized has been positron emission tomography (PET). Typically, this technique entails the following procedure.

First, a sugar derivative of glucose which has been labelled with a positron emitter and is in addition incapable of fueling the Embden-Meyerhof pathway, is obtained for use as a tracer material. The glucose derivative is injected into the body to be metabolically mapped. Since glucose is the basic fuel for energy of metabolism, and is absorbed by cells in proportion to metabolic activity, the result of injecting the glucose derivative into the body is that the glucose derivative accumulates in areas of high metabolic activity, for example, local areas within the brain. These areas of high metabolic activity, which then contain the labelled derivative, may be visualized by the use of positron emission tomography.

However, PET suffers from a number of serious disadvantages which, to cite a few, are:

(1) the positron emitter, having a short half life, must be produced by bombardment with a cyclotron;

(2) the emitter (usually $F^{18}$) must be attached to the glucose derivative chemically;

(3) since the emitter has a short half life, the cyclotron production and chemical coupling, and subsequent injection into the patient, must be performed rapidly, and this is very difficult since it requires the coordination of several specialists, and the cyclotron must be on-site with the patient and the PET instrument; and (4) there are less than 100 such PET scanners in the world, and therefore the technique is limited to a very few geographical locations.

Hence, a need continues to exist for a method for metabolic mapping of the mammalian central nervous system, which suffers from none of the disadvantages attendant to PET scanning, and which, moreover, provides a safe means for accomplishing the same.

SUMMARY OF THE INVENTION

Accordingly, it is an object of the present invention to provide a method for metabolic mapping of the central nervous system of a mammalian body.

It is, in particular, an object of this invention to provide a method for metabolic mapping of the central nervous system of a mammalian body by computerized axial tomography.

It is also an object of the present invention to provide certain radioopaque hexose derivatives which may be used in conjunction with the present method.

According to the present invention, the foregoing and other objects are attained by providing a method of metabolically mapping one or more components of the central nervous system of a mammalian body by computerized axial tomography, which entails injecting an effective amount of a 2-, 5- or 6-iodo-substituted hexose as a contrast medium into the mammalian body; and scanning the mammalian body in accordance with computerized axial tomography, thereby visualizing the concentration flux of the hexose in the central nervous system component or components.

DETAILED DESCRIPTION OF THE PREFERRED EMBODIMENTS

In accordance with the present invention, it has been found that it is possible to utilize 2-, 5- or 6-iodo-substituted hexoses as radioopaque contrast agents for metabolic mapping of one or more components of the mammalian central nervous system.

This pattern of substitution has been found to be important inasmuch as hydroxyl substitution appears necessary at the 1-, 3- and 4- positions of the hexose in order to ensure a sufficient degree of transport across the cell membrane for uptake.

The term "hexose" is, of course, defined as indicating monosaccharides containing six carbon atoms, such as glucose. Of course, the term "monosaccharide" is well-known and refers to a sugar not decomposable to simpler sugars by hydrolysis.

However, within the scope of the present invention are the 2-, 5- and 6-iodo-substituted hexoses. Within the hexose family can be mentioned the appropriately substituted allose, altrose, glucose, mannose, gulose, idose, galactose and talose. However, particularly worthy of mention are the respective glucose, galactose, mannose and allose compounds. Of these, the glucose and galactose are preferred.

With respect to nomenclature, it is noted that the above-described hexoses, such as 6- iodo-galactose are alternatively known, according to the present invention, as 6-iodo-d-galactose, 6-deoxy-6-iodo-D-galactose and 6-deoxy-6-iodo-α-D-galactopyranose. For example, The molecular structure of the radioopaque sugar derivative 6-iodo-6-deoxy-α-D-galactopyranose is as follows:

The hexose derivatives of the present invention are easily obtained. Their synthesis will now be illustrated with reference to galactose in the preparation of 6-iodo-galactose.

The parent compound, galactose, is reacted with acetone, $(CH_3)_2=O$ at room temperature for 36 hours in the presence of copper sulfate, $CuSO_4$, and sulfuric acid, $H_2SO_4$. The product is isolated as a pale amber syrup and is analyzed on thin layer chromatography. The copper sulfate is utilized as a catalyst for joining the acetone at carbon positions 1, 2, 3, and 4, and the hydroxyl groups at positions 1, 2, 3 and 4 of the galactose are blocked so that they are unreactive at future steps. The sulfuric acid is used to reduce the pH factor.

The remaining free hydroxyl group at carbon 6 is derivatized, that is, modified to form the p-toluenesulfonyl derivative by reaction with p-toluenesulfonylchloride in the presence of anhydrous pyridine at room temperature for 15 hours. The derivative is isolated in crystalline form and is then further purified, resulting in a yield of 50% with a melting point of 90°-91° C.

The purified derivative is then reacted with NaI in an anhydrous system, acetone, at 125° C. for 36 hours so as to replace the toluenesulfonyl with iodine, and to yield the iodo-substituted compound with a yield of 70% and a melting point of 70°-71° C.

The isopropylidine groups, the blocking groups, are removed from the derivative using trifluoroacetic acid at room temperature for 30 minutes. The final product is isolated in crystalline form with a yield of 45% and a melting point of 108°-111° C.

Other suitable hexose derivatives can be made in accordance with the above or analogous procedures.

The method of the present invention, as already noted, pertains to metabolically mapping one or more components of the central nervous system of a mammalian body by computerized axial temography by injecting an effective amount of a 2-, 5- or 6-iodo-substituted hexose as a contrast medium into the mammalian body; and scanning the mammalian body in accordance with computerized axial tomography, thereby visualizing the concentration flux of the hexose in the central nervous system components.

As a result of the implementation of the present method of metabolic mapping, the following advantages are achieved: (1) the contrast medium or compound can be prepared ahead of time; (2) a cyclotron is not needed, as in cases involving PET scanning; (3) chemists are not needed, for example, for combining the positron emitter with glucose as in the conventional method; (4) matters are, accordingly, quite simplified, as coordination between cyclotron personnel, chemists and other personnel is no longer needed; (5) there is no need for a PET scanner, with its complex composition and operation, not to mention the associated cyclotron which must be used therewith; and (6) a much finer resolution of the resulting image can be obtained by taking advantage of the inherently finer resolution of images resulting from CAT scanning vis-a-vis the less satisfactory resolution of images resulting from PET scannning.

Although 6-iodo-galactose has been used as an X-ray contrast agent, it is important to note that such use has uniformly involved only the gross visualization of organs with very little cell uptake. For example, U.S. Pat. Nos. 2,365,776 and 2,365,777 describe the use of 6-iodo-galactose as an X-ray contrast agent for the gross visualization of the kidney.

Such a technique relies upon the tendency of the kidney to concentrate 6-iodo-galactose, and, as such, is quite similar to the use of barium compounds in the visualization of the lower intestines.

The important point to note about such a technique, however, is that it is static in nature and is completely unrelated to the dynamic process of the present invention which, by virtue of monitoring the concentration flux of hexose uptake by the brain, for example, provides a valuable means of assessing the differential activities of structures within the brain.

Thus, the term "metabolic mapping" may now be seen to refer to a means by which it is possible to determine the rate of flux of hexose uptake into specific anatomical areas of interest. In accordance with the present invention, it is now possible to determine alterations in the rate of flux of hexose uptake into specific areas of the mammalian central nervous system, particularly the brain, in order to monitor the extent of activity in those areas.

As already noted, glucose derivatives are of use as they may be readily used as a fuel substance by the brain or other nervous tissue. However, other hexose derivatives, such as galactose, are converted to glucose in the liver. Moreover, while galactose does not directly undergo metabolism to meet brain cell energy requirements, it is required as a component of many oligosaccharides present in gangliosides, cerebrosides and cell membranes. Congenital deficiency of α-D-galactose-1-phosphate-uridyltransferase results in the accumulation of high cerebral galactose concentrations, indicating that there exist requisite mechanisms for transfer of galactose or other hexoses across the blood-brain barrier and into cerebral parenchyma. Hexose structral requirements necessary for binding of the carbohydrate to the RBC model sugar transport system have been determined and the carrier appears to be asymmetrical, i.e., different hydroxyl groups participate when the hexose is inside and outside the cell. Substitution of iodine for the hydroxyl group at the 2-, 5- or 6- position does not hamper cell uptake but does prevent its export. Hence, iodo-hexoses having iodine at each or all of these positions are used.

According to the present invention, injection has been found to be the best means of administering the hexose derivatives. However, other means of administering the same which are effective therefor may be used as equivalent to injection. Generally, about 0.02–2.1 g of hexose derivative per kg of mammalian body weight is used. Preferably, about 0.175–0.5 g per kg of body weight is used. More preferable still is the range of about 0.2–0.4 per kg of body weight.

It is noted that increased amounts of hexose contrast agent increase the intensity, but generally not the duration of the image.

In scanning the body, conventional operating techniques for the CAT scanner may be employed. As such, CAT scanning equipment and techniques for the operation thereof are well within the knowledge of those skilled in the art.

Injection of 6-IG (6-iodo-galactose) into mice, rats, and dogs in the concentrations described do not produce any obvious side effects. Dogs, for example, were required, and were able, to walk after injection of 6-IG and before they were anesthetized. The data presented in FIG. 2 indicate that the contrast medium accumulated in the cortical area of the posterior portion of the frontal lobe within one hour after injection. This is the region associated with limb and tail movement in the dog. In that time interval, accumulation, however, was incomplete, since greater contrast is seen in the same region 9 days post-injection. However, even at this later interval, no contrast is seen in the pareital lobe intracellular section shown in FIG. 3, nor in any other areas of the brain that were scanned. Thus, the accumulation can be made to be selective. Clearance of the compound is relatively slow, as the contrast medium was present at nine days post injection. Peak concentration, therefore, appears to have been achieved some time inbetween.

As compared to measurements of metabolic activity by PET scanning using Fluorodeoxyglucose (FDG), the accumulation and clearance of 6-IG is relatively slower and appears to be different from FDG. 6-IG probably enters the cell by sharing the glucose membrane transport system, and cellular uptake is some function of the ratio of 6-IG to glucose in the ECF and the fraction of 6-IG that shares the membrane carrier protein. Its use as an index of glucose utilization is not the same as FDG, but it is evident that it accumulates in areas of the brain that are metabolically hyperactive in response to normal stimuli. Therefore, the development and use of 6-IG and other suitable hexoses as a contrast medium is significant in that additional studies of brain function in normal and pathologic states are now possible.

The present invention will now be further illustrated by certain examples and references which are provided for purposes of illustration only and are not intended to limit the present invention.

EXAMPLE 6-iodo-6-deoxy-α-D-galactopyranose (6-IG) was prepared from 6-deoxy-6-iodo-1,2,3,4-di-O-isopropylidine α-D-galactopyranose (Pfanstiel Co.), by reaction with trifluoroacetic for 30 minutes at room temperature. The product gave a single spot when analyzed by thin-layer chromatography and identified by charring.

Gross Toxicology. In order to be economical with the product, the gross toxicology of 6-IG was first determined in mice and rats. Enough material was injected in a volume of 0.1 ml into the tail vein to raise the blood concentration to $10^{-3}$, $10^{-2}$, and $10^{-1}$M, (0.02–2.11 g/kg). As an osmotic control, equimolar amounts of α-D-galactopyranose were injected into age matched animals.

Scanning Methods

Mongrel dogs (40–50 lbs) were injected intravenously with a bolus of α-D-galactose sufficient to raise the blood concentration to a level of $10^{-2}$M. They were then required to walk from the animal facility to the CAT scanner, approximately 10 minutes, where they were anesthetized. Anesthesia was induced with thiamytal (lmg/kg) and the animal was intubated with a cuffed endotrachial tube. Following induction, anesthesia was maintained with a gaseous mixture of Halothane, nitrous oxide and oxygen.

The time elapsed from injection to the start of the scan was approximately 1 hour. CAT scanning data were recorded on tape and served as a background control. Upon completion of scanning, the dog was recovered from anesthesia and returned to the animal facility, where routine care was resumed.

This procedure was repeated one day later; however, 6-IG was injected to an initial blood concentration of $10^{-2}$M. Nine days and 33 days following the injection, repeat scans were performed to ensure that the contrast medium had cleared.

Results

6-IG was injected intravenously into 20 g male mice and equivalent amounts of α-D-galactopyranose were injected into age-matched controls. The injections (max 2.11 g 6-IG/kg) had no apparent immediate effects on the animals. Three days post-injection, the animals were killed by ether inhalation and autopsied. There were no gross findings.

Dogs were injected with either α-D-galactose or 6-IG in sufficient quantity to raise the initial blood concentration to $10^{-2}$M. It has been found that the detection level for iodine, as determined in phantom studies, using these scanning techniques, lies between $10^{-3}$ and $10^{-4}$M. Neither the control nor the iodinated injection medium had any apparent side effects on the animals.

Figure 1:
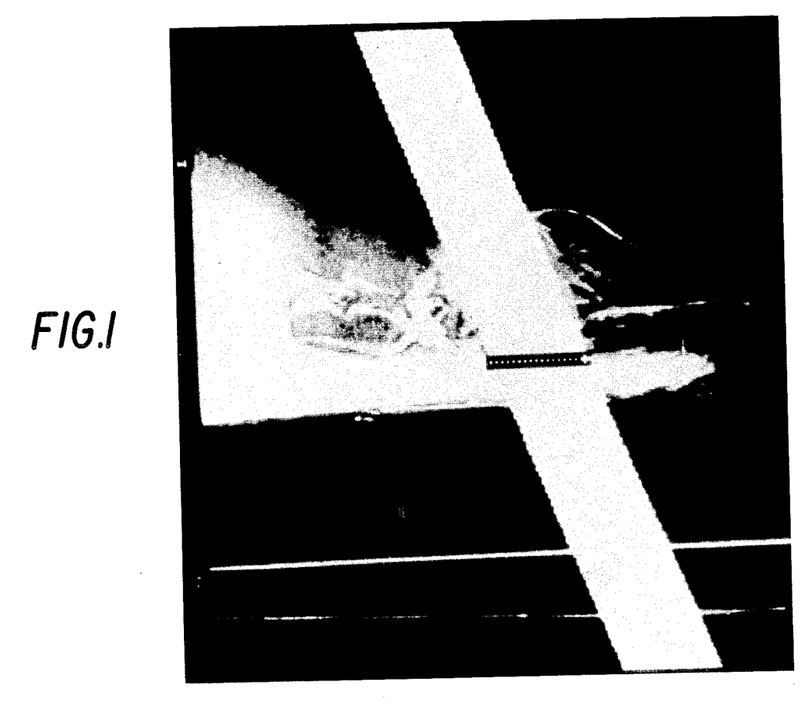
FIG. 1 shows a Scanagram of a dog brain. The arrow indicates the position of scans shown in FIG. 2.

The dog's brains were scanned by CAT in sequential slices in 3 mm. increments. FIG. 1 shows the plane of the traverse scan. The arrow indicates the regions where contrast was observed. FIG. 2 shows one of the slices of interest: (A) before injection of contrast medium, (B) 1 hour, (C) 9 days and (D) 33 days post-injection. Arrows in panel B indicate the beginning of accumulation as early as 1 hour post-injection. Accumulation is not, however, complete, as panel C indicates, where there is greater contrast in the same cortical regions. Panel D, taken 33 days post-injection indicates that the contrast medium has cleared completely.

Figure 2A:
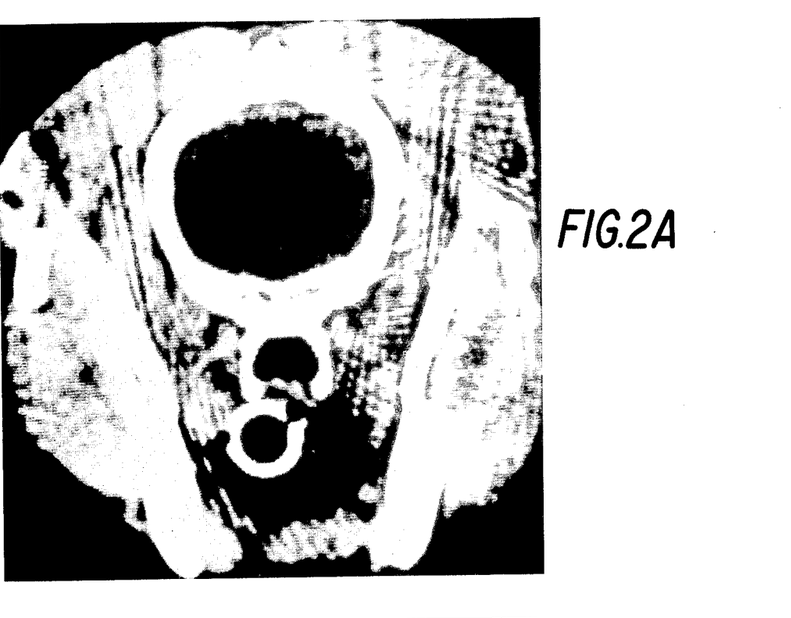
FIG. 2 shows a scan of a 3 mm-thick slice of a posterior portion of the frontal lobe (A) 24 hours before injection; (B) 1 hour post-injection; (C) 9 days post-injection; (D) 33 days post injection.
Figure 2B:
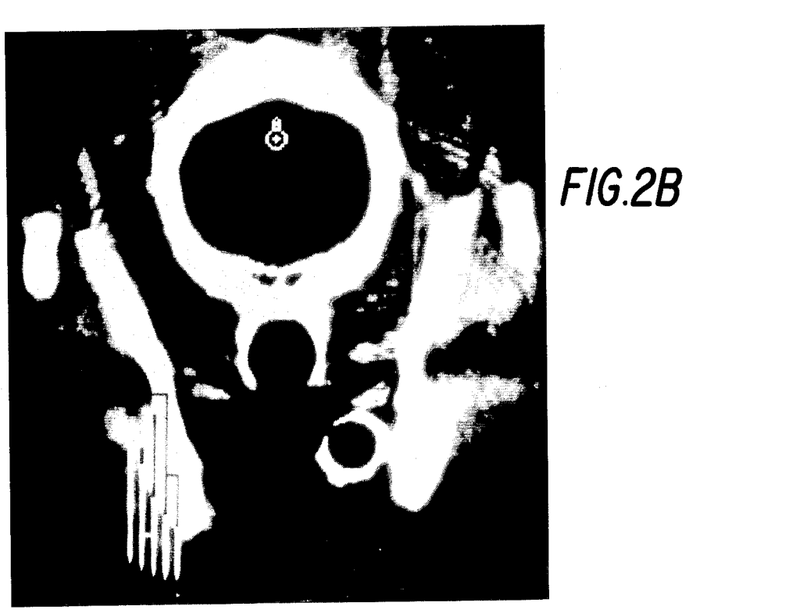
Figure 2C:
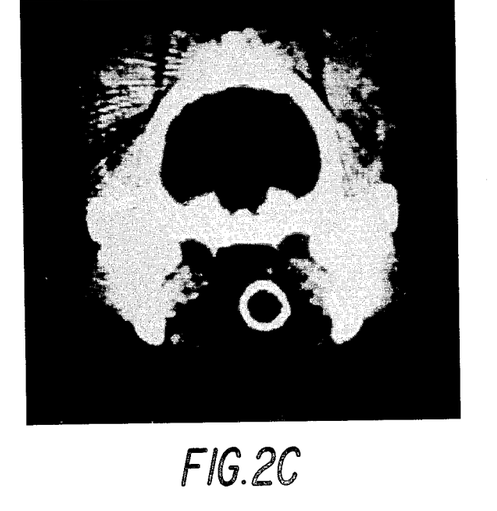
Figure 2D:
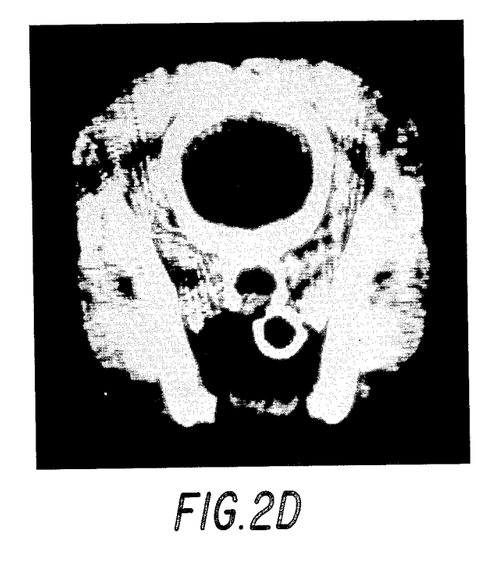
Figure 3:
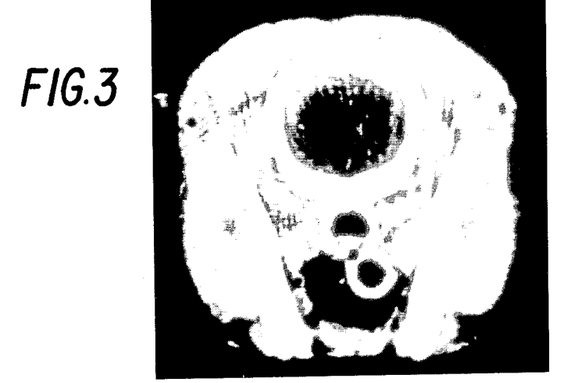
FIG. 3 shows a scan of a 3 mm-thick slice at 9 day post-injection of a posterior portion of the pareital region.

FIG. 3 represents a slice taken on the same day but more posterior to that shown in FIG. 2C. As was the case in other areas of the brain CT scan (anterior and posterior), it is seen that no contrast medium has accumulated in that section of the brain.

Figure 4:
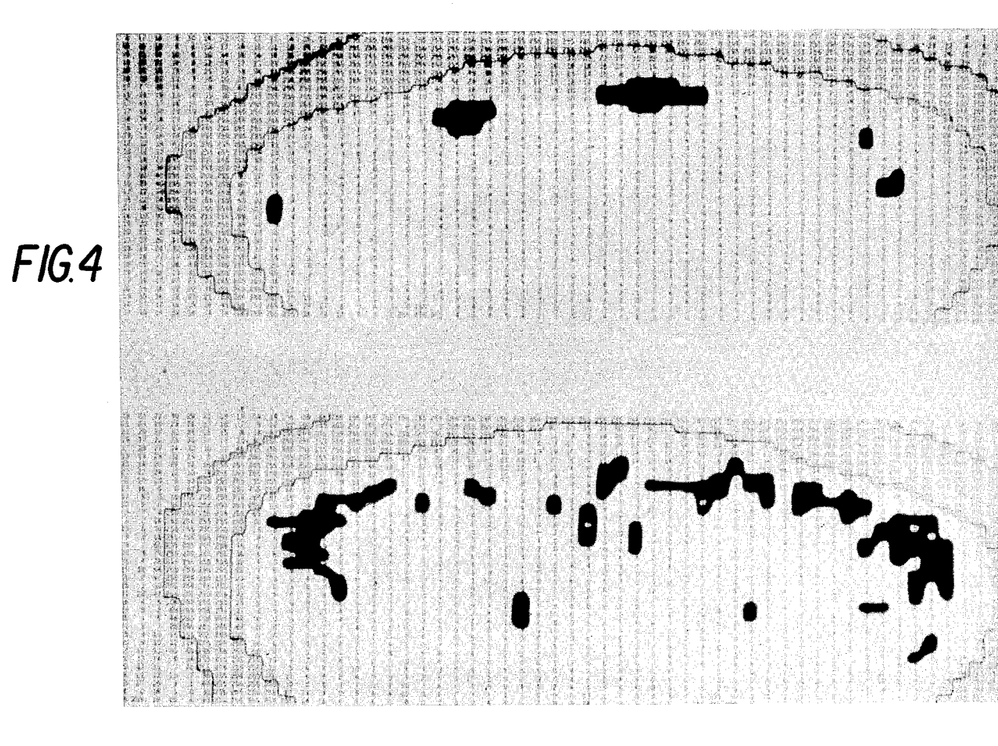
FIG. 4 Top: shows the Digitization of the slice shown in FIG. 2(D) (33 days post-injection). Bottom: shows the Digitization of the slice shown in FIG. 2(c) (9 days post). In each, the average background was subtracted out (140 gray level). Shaded areas indicate significant contrast.
Figure 5:
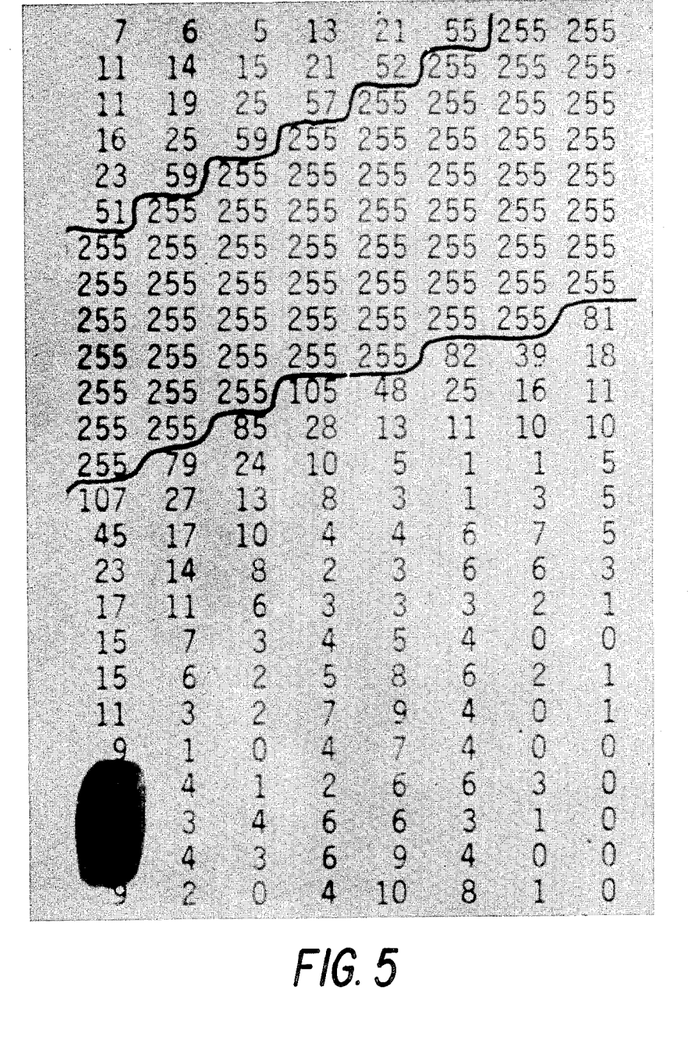
FIG. 5 shows an enlargement of the left side of FIG. 4, top.
Figure 6:
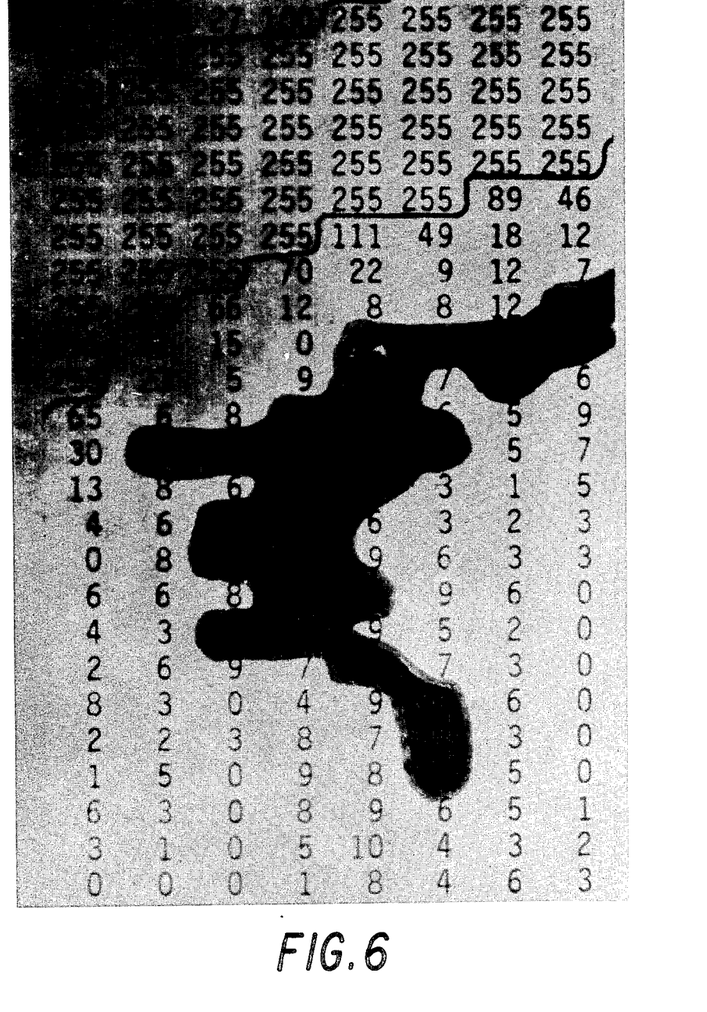
FIG. 6 shows an enlargement of the same area as FIG. 5 showing gray level intensity of FIG. 4, bottom.
Figure 7:
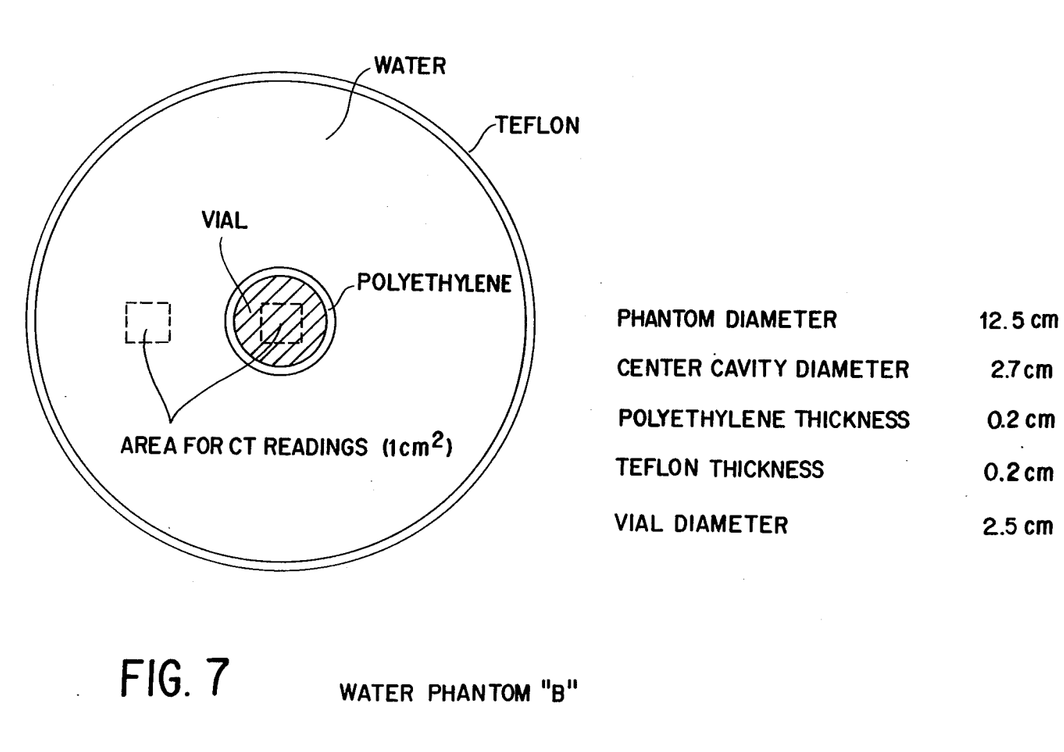
FIG. 7 shows a graph of a CT-X-ray attenuation as a function of iodine concentration. Closed circles iodine, open circles water blank.
Figure 8:
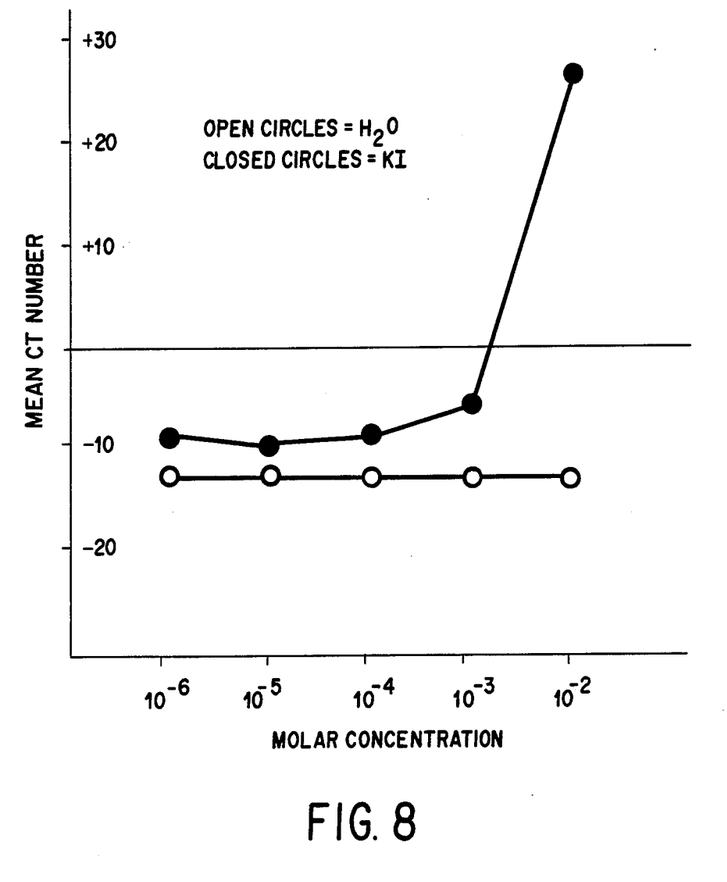
FIG. 8 shows a cross-section of a phantom used to obtain data in FIG. 7.
Figure 9:
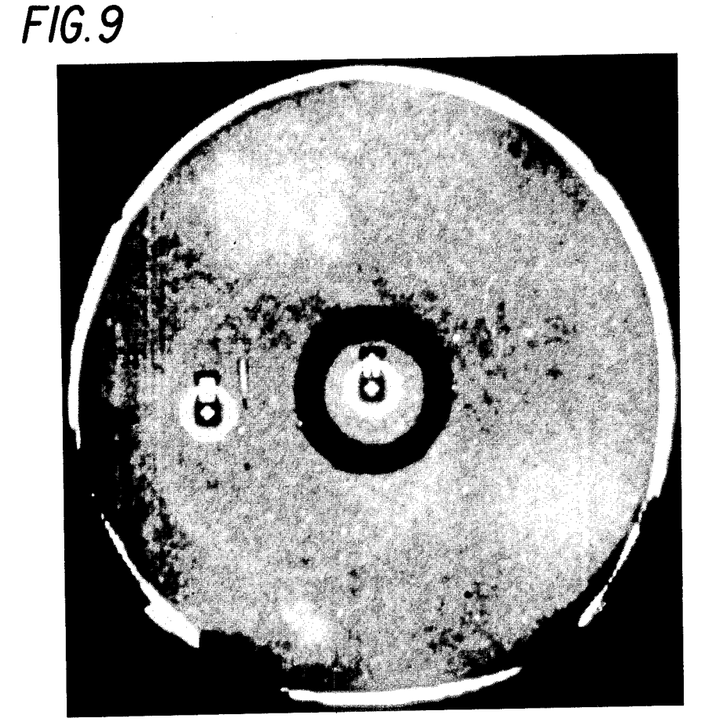
FIG. 9 shows an example of a CT scan of a Phantom depicted in FIG. 8.

The slice shown in FIG. 2C was chosen for computerized digitization and pattern analysis. FIG. 4 shows a digitized, complementary image of this slice from which an average background has been subtracted. Areas of significant contrast have been shaded. The accumulation is generally greatest in the cortical region, although other areas are certainly significant and subject to analysis.

Feasibility Calculations

It has been found that the detection limit for iodine using current CAT scanning techniques lies between the concentrations of about $10^{-4}$ and $10^{-3}$M. However, dual energy methods appear to enhance sensitivity. It appears feasible to achieve such concentrations in, for example, brain tissue, by administering a sufficient amount of 6-iodo-D-galactose to obtain an initial blood concentration of about $10^{-2}$M in the patient. This is demonstrated by the following calculations, which are based on data and parameters supplied by researchers doing PET scanning.

For FDG, the observed concentration in the brain is 20% of the initial blood concentration. This is demonstrated as follows. When 0.5 mg of FDG is injected in the approximately 4–5 L blood volume of a human, an initial blood concentration of $6.9 \times 10^{-7}$ M results:

$$\frac{0.5 \text{ mg}}{4 \text{ L}} = \frac{1.25 \times 10^{-4} \text{ g}}{\text{L}} \times \frac{\text{mol}}{180 \text{ g}} = 6.9 \times 10^{-7} \text{ M}$$

Also, from the 0.5 mg FDG injection, a brain concentration of 25 ng/cc is observed after 40 minutes accumulation time. This is equivalent to a molar brain concentration of $1.38 \times 10^{-7}$M, given that the human adult brain has a cell volume of 1 L.

$$\frac{25 \text{ ng}}{\text{cc}} = \frac{25 \ \mu\text{g}}{\text{brain}} = \frac{2.5 \times 10^{-5} \text{ g}}{\text{L}} \cdot \frac{\text{mol}}{180 \text{ g}} = 1.30 \times 10^{-7} \text{ M}$$

Thus, we have $$\frac{\text{brain concentration}}{\text{blood concentration}} = \frac{1.3 \times 10^{-7} \text{ M}}{6.9 \times 10^{-7} \text{ M}} \cdot 100 = 20\%$$

However, it is proposed to use 6-iodo-D-galactose or other such 2-, 5- or 6-substituted hexoses. Both 2-deoxyglucose and D-galactose cross the blood/brain barrier by the same saturable carrier as glucose. But the uptake of galactose relative to 2-deoxyglucose is 31%. Therefore, it is estimated that the total brain concentration of 6-iodo-D-galactose is approximately 20% × 0.31, or 6% of the initial blood concentration. When the initial blood concentration is $10^{-2}$M, final brain concentration would approximate $6 \times 10^{-4}$M. To achieve this, it is necessary to inject approximately 15 grams of iodogalactose.

$$\text{wt} = (5 \text{ liter}) \left( 1 \times 10^{-2} \frac{\text{mole}}{\text{liter}} \right) \left( 290 \frac{\text{g}}{\text{mole}} \right) = 14 \text{ g}$$

An adult has a blood volume of approximately 4–5 L, so to achieve the desired concentration of $10^{-2}$M (moles per liter) of 6-iodo-galactose whose formula weight is 290 g/mole will require:

wt = (5 liter)(1 × $10^{-2}$ mole/liter)(290 g/mole) = 14 g.

Thus, the criterion of having a brain concentration within the range of $10^{-4}$ to $10^{-3}$ M is met. Although this concentration is the lower limit of detection, it should not deleteriously affect the clarity of the brain CAT scan. It should be emphasized that the desired brain concentration should be at least at threshold of detection, that is, in the range of $10^{-4}$ to $10^{-3}$M. This should not be taken to mean that structural detail will be visualized at these levels. Rather, this is an average level. Accumulations, which therefore have local concentrations appreciably greater than this, will be contrasted against a zero background, since the average brain is at the threshold concentration. If metabolically active brain areas acquire a two- to three-fold greater amount of contrast agent, either metabolically or by injecting a three-fold higher dose of 42 gms., these foci will then contrast well within the limits of detectability. Unlike PET scan-mapping which requires continuous stimulation beginning five minutes before administration: the 40–45 minutes post IV and the 30 minutes required for pet scanning. This long period of stimulation would not be required for the hexoses of the present invention, a local concentration of 5uM/gm of tissue is easily seen.

It should be noted that depending upon the particular area of interest in the central nervous system, differing amounts of contrast medium may be required. For example, while a certain concentration may indicate a selective accumulation in the critical regions of the brain, an increased concentration would also permit visualization of other areas of the brain such as the anterior or posterior portions.

Moreover, as noted, it is also possible to use the method of the present invention to study the spinal system. In particular, as the hexoses of the present invention are taken up by nervous tissue, in general, it is possible to study individual structures within the brain and the spinal system during the same injection-scan sequence.

Additionally, the amounts of contrast medium used are dependent upon the actual imaging techniques utilized in visualizing the central nervous system components. For example, it might, indeed, be possible to use less contrast agent when using a new reconstruction technique such as a back-projection technique as opposed to a conventional reconstruction technique.

Having now fully described this invention, it will be apparent to one of ordinary skill in the art that many changes and modifications can be made thereto without departing from the spirit or scope of the invention as set forth herein.

What is claimed and desired to be secured by United States Letters Patent is:

1. A method of metabolically mapping one or more central nervous system components of a mammalian body by computerized axial tomography scanning which comprises:
   (a) injecting an effective amount of a 2-,5-, or 6-iodo-substituted hexose, as a contrast medium, into said mammalian body, and
   (b) scanning the mammalian body by computerized axial tomography, thereby visualizing the concentration flux of said hexose in the central nervous system component or components.

2. The method of claim 1, wherein said hexose is a glucose, galactose, mannose or allose.

3. The method of claim 1, wherein said hexose is 6-iodo-galactose.

4. The method of claim 1, wherein an amount of said hexose is injected sufficient to obtain an initial blood concentration of at least about $10^{-2}M$ in said mammalian body.

5. The method of claim 1, wherein said hexose is injected in the amount of about 0.175 grams to 0.50 grams per kilogram of mammalian body weight.

6. The method of claim 1, wherein said mammal is a human.

7. The method of claim 1, wherein said central nervous system components comprise the brain or the spinal cord or a combination thereof.

8. The method of claim 7, wherein said central nervous system component comprises the brain.

9. The method of claim 8, wherein said central nervous system component comprises the cortical regions of the brain.

10. The method of claim 8, wherein said central nervous system component comprises the cortical area of the posterior portion of the frontal lobe of the brain.

11. A method of metabolically mapping a human brain by computerized axial tomography, which comprises:
   (a) injecting an effective amount of a 2-, 5- or 6-iodo-substituted hexose, as a contrast medium, into said mammalian body, and
   (b) scanning the mammalian body by computerized axial tomography, thereby visualizing the concentration flux of said hexose in the brain.

12. The method of claim 11, wherein said hexose is a glucose, galactose, mannose or allose.

13. The method of claim 11, wherein said hexose is 6-iodo-galactose.

14. The method of claim 11, wherein an amount of said hexose is injected sufficient to obtain an initial blood concentration of at least about $10^{-2}M$ in said mammalian body.

15. The method of claim 11, wherein an amount of said hexose is injected sufficient to obtain a brain concentration of about $10^{-4}M$ to $10^{-3}M$.

16. A method of metabolically mapping one or more central nervous system components of a mammalian body by computerized axial tomography scanning which comprises:
   (a) injecting an effective amount of a 2-, 5-, or 6-iodo-substituted glucose or galactose, as a contrast medium, into said mammalian body, and
   (b) scanning the mammalian body by computerized axial tomography, thereby visualizing the concentration flux of said glucose or galactose in the central nervous system component or components.

17. A method of metabolically mapping a human brain by computerized axial tomography, which comprises:
   (a) injecting an effective amount of a 2-, 5-, or 6-iodo-substituted glucose or galactose, as a contrast medium, into a human body, and
   (b) scanning the human brain by computerized axial tomography, thereby visualizing the concentration flux of said glucose or galactose in the brain.

18. A 2- or 5-iodo-substituted hexose, wherein said hexose is selected from the group consisting of glucose, and galactose.

19. A 2-, 5- or 6-iodo-substituted hexose, wherein said hexose is selected from the group consisting of allose, altrose, mannose, gulose, idose, and talose.

* * * * *

UNITED STATES PATENT AND TRADEMARK OFFICE
CERTIFICATE OF CORRECTION

PATENT NO.　：　4,716,225
DATED　　　：　DECEMBER 29, 1987
INVENTOR(S)：　ROBERT S. LEDLEY ET AL

It is certified that error appears in the above-identified patent and that said Letters Patent is hereby corrected as shown below:

Column 3, line 58, change "$(CH_3)_2=O$" to --$(CH_3)_2C=O$--;

Column 3, line 62, delete "copper sulfate is utilized as a catalyst for joining the";

Column 3, line 63, delete "acetone at carbon positions 1, 2, 3, and 4, and the".

Column 5, line 64, change "inbetween" to --in between--.

Column 9, line 23, change "$10-2M$" to --$10^{-2}$ M--.

Signed and Sealed this

Twenty-fifth Day of June, 1991

Attest:

HARRY F. MANBECK, JR.

*Attesting Officer*　　Commissioner of Patents and Trademarks